United States Patent
Reis

(10) Patent No.: US 6,255,123 B1
(45) Date of Patent: Jul. 3, 2001

(54) METHODS OF MONITORING AND MAINTAINING CONCENTRATIONS OF SELECTED SPECIES IN SOLUTIONS DURING SEMICONDUCTOR PROCESSING

(76) Inventor: Kenneth P. Reis, 10014 Tezel Rd., San Antonio, TX (US) 78250

( * ) Notice: Subject to any disclaimer, the term of this patent is extended or adjusted under 35 U.S.C. 154(b) by 0 days.

(21) Appl. No.: 09/193,549

(22) Filed: Nov. 17, 1998

(51) Int. Cl.[7] .................................................. H01L 21/306
(52) U.S. Cl. ................................. 438/8; 438/757; 216/85
(58) Field of Search .................................. 216/85; 438/8, 438/16, 757, FOR 101, FOR 141

(56) References Cited

U.S. PATENT DOCUMENTS

| | | | |
|---|---|---|---|
| 4,731,154 | * | 3/1988 | Hausman Hazlitt et al. . |
| 5,403,433 | * | 4/1995 | Morrison et al. . |
| 5,437,761 | * | 8/1995 | Koide . |
| 5,595,916 | * | 1/1997 | Fujimura et al. . |
| 5,674,410 | * | 10/1997 | Nakajima et al. . |
| 5,922,606 | * | 7/1999 | Jenkins et al. . |
| 5,963,336 | * | 10/1999 | McAndrew et al. . |
| 6,077,452 | * | 6/2000 | Litvak . |

* cited by examiner

Primary Examiner—George Fourson
Assistant Examiner—Joannie Adelle Garcia
(74) Attorney, Agent, or Firm—Wells, St. John, Roberts, Gregory & Matkin

(57) ABSTRACT

In one aspect, the invention encompasses a semiconductor processing method. A layer of material is provided over a substrate and reacted in a solution to remove at least some of the material. The reacting comprises a reaction chemistry that alters a concentration of a species in the solution. An absorbance of the solution is monitored for at least one wavelength of light that the species absorbs, and a concentration of the species in the solution is monitored by the monitoring of the absorbance. The concentration of the species in the solution is adjusted utilizing information obtained from the absorbance monitoring.

In another aspect, the invention encompasses a semiconductor processing method wherein a layer of material is provided over a substrate and reacted with a solution to remove at least some of the material. The reaction consumes a component of the solution, and an absorbance of the solution is monitored for at least one wavelength of light that the consumed component absorbs. The concentration of consumed component in the solution is monitored during the reaction by monitoring the absorbance. The consumed component is added to the solution to maintain a substantially constant rate of reaction during the removal of the first material.

29 Claims, 1 Drawing Sheet

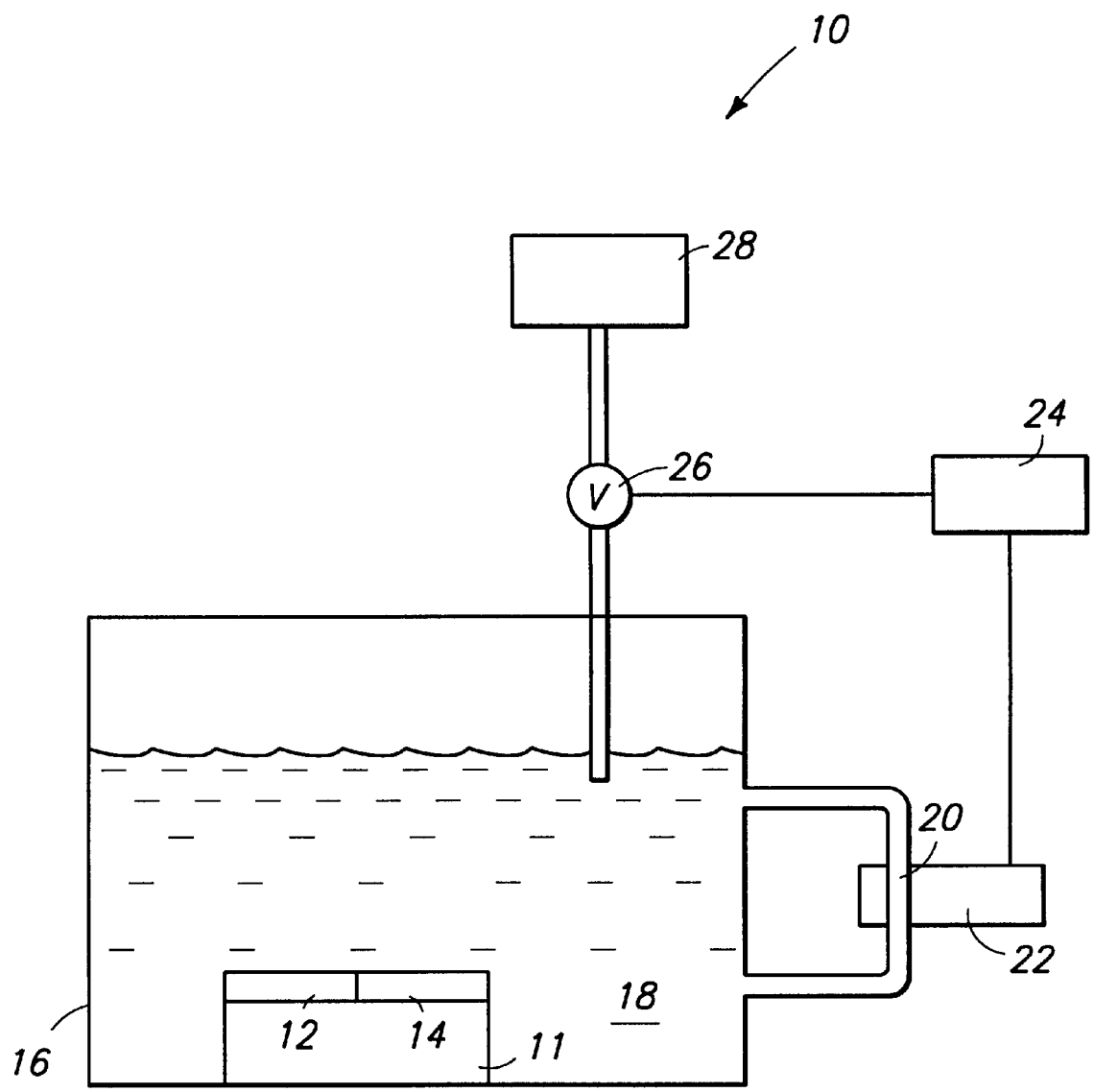

METHODS OF MONITORING AND MAINTAINING CONCENTRATIONS OF SELECTED SPECIES IN SOLUTIONS DURING SEMICONDUCTOR PROCESSING

TECHNICAL FIELD

The invention pertains to methods of monitoring and maintaining concentrations of selected species in solutions during semiconductor processing, with the term "solution" referring to any fluid, including, for example, a liquid or a gas. In a particular aspect, the invention pertains to methods of monitoring and maintaining a predetermined water concentration in phosphoric acid solutions during etching of silicon nitride.

BACKGROUND OF THE INVENTION

Modern semiconductor processing frequently utilizes etchant removal of selected materials. For instance, a common insulative material in semiconductor circuitry is silicon nitride ($Si_3N_4$), which is typically patterned into desired configurations by etching processes. A typical etching process for removing silicon nitride comprises exposing the silicon nitride to a liquid phosphoric acid solution. A phosphoric acid solution etch of silicon nitride has a particular advantage in that it is generally selective for silicon nitride relative to silicon dioxide. Accordingly, if both silicon nitride and silicon dioxide are exposed to the conditions of a phosphoric acid solution etch, the silicon nitride will be removed at a faster rate than will the silicon dioxide.

The reaction chemistry of a phosphoric acid solution etch of silicon nitride is as follows:

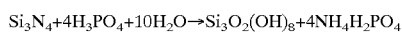

$$Si_3N_4 + 4H_3PO_4 + 10H_2O \rightarrow Si_3O_2(OH)_8 + 4NH_4H_2PO_4$$

As can be seen from the above equation, water is a reactant that is consumed during etching of the silicon nitride with the phosphoric acid solution. The reaction conditions of the etch typically comprise a temperature of from about 150° C. to about 170° C., and typically comprise a pressure of about atmospheric pressure.

Under the typical etching conditions, a water concentration within the phosphoric acid solution can be reduced by water evaporation, as well as by water being consumed in the reaction process. Problems occur as a water concentration within the phosphoric acid solution decreases. For instance, a reaction rate can slow (or even stop) if water is not replenished. In an effort to overcome this problem, water (typically in the form of deionized water) is generally replaced at selected times, or selected temperature drifts, during a reaction process. Present methods for replacing deionized water have several associated problems, including: 1) it is difficult to accurately control etch rates; 2) the deionized water concentration in a reaction solution is not known, and accordingly a reaction rate can vary significantly from a beginning of a reaction to an end of the reaction; and 3) if an error occurs in a water replenishment mechanism and water is inadvertently not replenished at various points in a reaction process, the problem will not be detected until product wafers are removed and found to have an incomplete nitride strip.

For the above-discussed reasons, it would be desirable to develop alternative methods for maintaining a water concentration in a phosphoric acid solution during a nitride etch. More generally, it would be desirable to develop alternative methods for maintaining concentrations of selected species in solutions during semiconductor fabrication processes.

SUMMARY OF THE INVENTION

In one aspect, the invention encompasses a semiconductor processing method. A layer of material is provided over a substrate and reacted in a solution to remove at least some of the material. The reacting comprises a reaction chemistry that alters a concentration of a species in the solution. An absorbance of the solution is monitored for at least one wavelength of light that the species absorbs, and a concentration of the species in the solution is monitored by the monitoring of the absorbance. The concentration of the species in the solution is adjusted utilizing information obtained from the absorbance monitoring.

In another aspect, the invention encompasses a semiconductor processing method wherein a layer of material is provided over a substrate and reacted with a solution to remove at least some of the material. The reaction consumes a component of the solution, and an absorbance of the solution is monitored for at least one wavelength of light that the consumed component absorbs. The concentration of the consumed component in the solution is monitored during the reaction by monitoring the absorbance. The consumed component is added to the solution to maintain a substantially constant rate of reaction during the removal of the first material.

BRIEF DESCRIPTION OF THE DRAWING

The FIGURE is a diagrammatic, schematic, cross-sectional view of an apparatus configured for a processing a semiconductor wafer in accordance with an aspect of the present invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In one aspect, the invention encompasses a method of monitoring a water concentration during a liquid phosphoric acid solution etch of silicon nitride. The water concentration is monitored spectroscopically by monitoring an absorbance of the phosphoric acid solution for at least one wavelength of light that water absorbs. An exemplary wavelength is 1380 nanometers. If a suitable wavelength is chosen wherein only water absorbs, the absorbance at such wavelength will be proportional to the concentration of water within the solution. Specifically, it is known that A=Kcb, wherein A equals a spectroscopic absorbance, K equals a constant, c equals the concentration of the absorbing species, and b equals the pathlength of light through the absorbing species. If b and K are known, a concentration of water can be precisely determined. However, it is not necessary to know either of b or K to practice a method of the present invention. Rather, simply knowing that the absorbance at the wavelength is proportional to water concentration can enable a person to monitor changes in water concentration by monitoring changes in absorbance at the chosen wavelength.

If a wavelength is chosen wherein other components of the phosphoric acid solution absorb in addition to water, changes in absorbance will still reflect changes in water concentration but will not necessarily be directly proportional to changes in water concentration. Instead, the changes in absorbance may reflect changes in water concentration and changes in concentrations of other species absorbing at the monitored wavelengths. Ideally, the monitored wavelengths will be chosen such that the observed changes are at least primarily due to changes in water concentration. At such wavelengths, changes in absorbance will be at least approximately proportional to changes in water concentration.

Systems for monitoring absorbance of a phosphoric acid solution during reaction of silicon nitride with the solution can be readily constructed by persons of ordinary skill in the art. Such systems can involve, for example, discontinuous monitoring of the absorbance of the solution. A system for discontinuous monitoring of such absorbance can comprise, for example, a system in which aliquots of solution are removed at predetermined time intervals and spectrometrically analyzed. Alternatively, the systems for monitoring absorbance of a phosphoric acid solution can comprise continuous monitoring of the absorbance of the solution. An exemplary system for continuous monitoring comprises a flow cell in a spectrometer. At least a portion of the monitored solution is continuously passed through the flow cell during reaction of the phosphoric acid solution with silicon nitride. A system 10 configured to continuously monitor the absorbance of a liquid phosphoric acid solution during reaction of the solution with silicon nitride is described with reference to the FIGURE.

A semiconductor substrate 11 (which can comprise, for example, monocrystalline silicon) having silicon nitride material 12 and silicon dioxide material 14 formed thereover, is provided in a reaction vessel 16. To aid in interpretation of this disclosure and the claims that follow, the term "semiconductive substrate" is defined to mean any construction comprising semiconductive material, including, but not limited to, bulk semiconductive materials such as a semiconductive wafer (either alone or in assemblies comprising other materials thereon), and semiconductive material layers (either alone or in assemblies comprising other materials). The term "substrate" refers to any supporting structure, including, but not limited to, the semiconductive substrates described above.

A phosphoric acid solution 18 is also provided in reaction vessel 16. Layers 12 and 14 are exposed to the phosphoric acid solution to etch silicon nitride of layer 12 selectively relative to the silicon dioxide of layer 14. During the reaction of the silicon nitride of layer 12 with phosphoric acid solution 18, a portion of the phosphoric acid solution is flowed into a flow cell 20 and through a spectrometer 22 to monitor an absorbance of the solution at a wavelength of light that is absorbed by water. A signal from spectrometer 22 is passed to a microprocessor 24 configured to monitor the absorbance at the wavelength of light, and to thereby monitor a concentration of water within solution 18. Microprocessor 24 controls a valve 26 which is located between a deionized water source 28 and solution 18. As microprocessor 24 detects the absorbance falling, the microprocessor opens valve 26 to allow water from source 28 to flow into solution 18. Microprocessor 24 can then close valve 26 when the absorbance reaches a predetermined value. Accordingly, microprocessor 24 can maintain a predetermined concentration of water within solution 18, and can thereby maintain a predetermined rate of reaction of solution 18 with the silicon nitride material 12. In an exemplary application, system 10 is configured to maintain a concentration of water within phosphoric acid solution 18 at from about 5% to about 20% (preferably about 10%) (by weight), which maintains a rate of removal of silicon nitride at from about 10 Å/minute to about 100 Å/minute (preferably about 50 Å/minute) at a temperature of about 160° C.

Although the invention is described above with reference to an exemplary process for maintaining a water concentration in a phosphoric acid solution during reaction with silicon nitride, it is to be understood that the invention is not limited to such exemplary process. For instance, other processes are known wherein a material is reacted with a solution to remove at least some of the material, and wherein the reacting alters the concentration of a species in the solution. A method of the present invention can be utilized in such other processes to monitor an absorbance of the solution for at least one wavelength of light that the species absorbs, and adjust a concentration of the species in the solution to, for example, maintain a substantially constant rate of reaction during the removing of the material. Exemplary semiconductor fabrication processes in which a method of the present invention can be utilized for monitoring a concentration of a species in a solution include cleaning processes (such as washing and rinsing processes) and etching process other than the above-discussed phosphoric acid etch, such as, for example, chemical-mechanical etch processes.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A semiconductor substrate processing method comprising:

providing a layer of material over the substrate;

providing the substrate having the layer of material into a reaction vessel;

reacting the material in a solution contained in the reaction vessel under conditions that alter a concentration of a species in the solution;

monitoring an absorbance of the solution for at least one wavelength of light that the species absorbs;

monitoring a concentration of the species in the solution during the reacting by monitoring the absorbance; and adding the species to the reaction vessel to adjust the concentration of the species in the solution.

2. The method of claim 1 wherein the adjusting comprises adding an additional amount of the species to the solution.

3. A semiconductor processing method comprising:

providing a layer of material over a substrate;

reacting the material in a solution contained in a reaction vessel to remove at least some of the material, the reacting comprising a reaction chemistry that alters a concentration of a species in the solution;

monitoring an absorbance of the solution for at least one wavelength of light that the species absorbs;

monitoring a concentration of the species in the solution during the reacting by monitoring the absorbance; and adding an amount of the species to the reaction vessel to adjust the concentration of the species in the solution.

4. The method of claim 3 wherein the adjusting maintains a substantially constant rate of reaction during the removing of the material.

5. The method of claim 3 wherein the absorbance is approximately proportional to the concentration of the species.

6. The method of claim 3 wherein the species is a reactant of the reaction chemistry.

7. The method of claim 3 wherein the material comprises silicon nitride, the solution comprises phosphoric acid, and the species is water.

8. The method of claim 3 wherein the substrate comprises monocrystalline silicon, the material comprises silicon nitride, the solution comprises phosphoric acid, and the species is water.

9. A semiconductor processing method comprising:
providing a layer of material over a substrate;
reacting the material with a solution to remove at least some of the material, the reaction consuming a component of the solution;
monitoring an absorbance of the solution for at least one wavelength of light that the consumed component absorbs;
monitoring the concentration of the consumed component in the solution during the reacting by monitoring the absorbance; and
adding the consumed component to the solution to maintain a substantially constant rate of reaction during the removing of the material.

10. The method of claim 9 wherein the absorbance is approximately proportional to the concentration of the consumed component.

11. The method of claim 9 wherein the material comprises silicon nitride, the solution comprises phosphoric acid, and the consumed component is water.

12. A processing method comprising:
exposing a layer of silicon nitride to a phosphoric acid solution, the phosphoric acid solution comprising water;
reacting the silicon nitride with the phosphoric acid solution at a rate;
monitoring an absorbance of the phosphoric acid solution for at least one wavelength of light that water absorbs;
monitoring the concentration of water within the phosphoric acid solution during the reacting by monitoring the absorbance; and
adding water to the phosphoric acid solution to maintain the rate at from about 10 Å/minute to about 100 Å/minute.

13. The method of claim 12 wherein the reacting occurs at a temperature of about 160° C.

14. The method of claim 12 wherein the adding occurs during the monitoring and reacting.

15. The method of claim 12 wherein the at least one wavelength includes 1380 nanometers.

16. The method of claim 12 further comprising, before the reacting, forming the layer of silicon nitride over a semiconductor substrate; and wherein the reacting occurs while the silicon nitride is over the semiconductor substrate.

17. The method of claim 16 wherein the semiconductor substrate comprises monocrystalline silicon.

18. The method of claim 16 further comprising, before the reacting, forming a layer of silicon dioxide over the substrate; wherein both the silicon dioxide and the silicon nitride are exposed to the phosphoric acid solution, and wherein the silicon nitride reacts at a faster rate than the silicon dioxide so that the silicon nitride is removed selectively relative to the silicon dioxide.

19. A processing method comprising:
exposing a layer of silicon nitride to a phosphoric acid solution, the phosphoric acid solution comprising water;
reacting the silicon nitride with the phosphoric acid solution;
monitoring an absorbance of the phosphoric acid solution for at least one wavelength of light that water absorbs;
monitoring the concentration of water within the phosphoric acid solution during the reacting by monitoring the absorbance; and
adding water to the phosphoric acid solution to maintain the concentration of water at from about 5% to about 20% (by weight), as determined by the absorbance monitoring.

20. The method of claim 19 wherein the adding occurs during the monitoring and reacting.

21. The method of claim 19 wherein the at least one wavelength includes 1380 nanometers.

22. The method of claim 19 further comprising, before the reacting, forming the layer of silicon nitride over a semiconductor substrate; and wherein the reacting occurs while the silicon nitride is over the semiconductor substrate.

23. The method of claim 22 wherein the semiconductor substrate comprises monocrystalline silicon.

24. The method of claim 22 further comprising, before the reacting, forming a layer of silicon dioxide over the substrate; wherein both the silicon dioxide and the silicon nitride are exposed to the phosphoric acid solution, and wherein the silicon nitride reacts at a faster rate than the silicon dioxide so that the silicon nitride is removed selectively relative to the silicon dioxide.

25. A method of removing silicon nitride comprising:
exposing a layer of silicon nitride to a phosphoric acid solution, the phosphoric acid solution comprising water;
reacting the silicon nitride with phosphoric acid and water from the phosphoric acid solution to form products that are soluble in the phosphoric acid solution and thereby removing at least some of the layer of silicon nitride;
monitoring an absorbance of the phosphoric acid solution for at least one wavelength of light that water absorbs;
monitoring the concentration of water within the phosphoric acid solution during the reacting by monitoring the absorbance; and
during the monitoring and reacting, adding water to the phosphoric acid solution to maintain the concentration of the water at from about 5% to about 20% (by weight).

26. The method of claim 25 wherein the at least one wavelength includes 1380 nanometers.

27. A method of removing silicon nitride comprising:
exposing a layer of silicon nitride to a phosphoric acid solution, the phosphoric acid solution comprising water;
reacting the silicon nitride with phosphoric acid and water from the phosphoric acid solution to form products that are soluble in the phosphoric acid solution and thereby removing at least some of the layer of silicon nitride;
monitoring an absorbance of the phosphoric acid solution for at least one wavelength of light that water absorbs;
monitoring the concentration of water within the phosphoric acid solution during the reacting by monitoring the absorbance; and
during the monitoring and reacting, adding water to the phosphoric acid solution to maintain a rate of removal of the silicon nitride at from about 10 Å/minute to about 100 Å/minute.

28. The method of claim 27 wherein the reacting occurs at a temperature of about 160° C.

29. The method of claim 27 wherein the at least one wavelength includes 1380 nanometers.

* * * * *